US007078220B2

(12) United States Patent
Greener et al.

(10) Patent No.: US 7,078,220 B2
(45) Date of Patent: Jul. 18, 2006

(54) HIGHLY TRANSFORMABLE BACTERIAL CELLS AND METHODS FOR PRODUCING THE SAME

(75) Inventors: Alan Lewis Greener, San Diego, CA (US); Bruce Douglas Jerpseth, San Diego, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 10/800,389

(22) Filed: Mar. 12, 2004

(65) Prior Publication Data
US 2004/0241861 A1 Dec. 2, 2004

Related U.S. Application Data

(63) Continuation of application No. 08/846,996, filed on May 1, 1997, now Pat. No. 6,706,525.

(51) Int. Cl.
*C12N 1/20* (2006.01)

(52) U.S. Cl. .............................. 435/252.2; 435/253.8; 435/252.8

(58) Field of Classification Search ................ 975/471, 975/252.33, 252.1
See application file for complete search history.

(56) References Cited

U.S. PATENT DOCUMENTS 6,706,525 B1 * 3/2004 Greener et al. ............. 435/471

OTHER PUBLICATIONS

Hanahan et al., "Plasmid transformation of *Escherichia-coli* and other bacteria," Methods in Enzymology, 204:63-113 (1991).
Likahacheva et al., "Induction of mutants of *Escherichia-coli* K-12 with increased efficiency of plasmid transformation," Byulleten' Eksperimental 'Noi Biologii I Meditsiny, 93 (5):81-82 (1982).
Radnis et al., "Genetic transformation in *Streptococcus pneumoniae*: nucleotide sequence and predicted amino acid sequence of *recP*," Journal of Bacteriology, 172 (1):3669-3674 (1990).

* cited by examiner

*Primary Examiner*—Nancy Vogel
(74) *Attorney, Agent, or Firm*—Finnegan, Henderson, Farabow, Garrett & Dunner, L.L.P.

(57) ABSTRACT

The invention provided herein includes novel gram negative bacteria cells containing the Hte mutation. Other aspects of the invention include methods for rendering gram negative bacterial cells bearing the Hte region, such as *E. coli* cells competent for DNA transformation using any of a variety of competency inducing procedures. The competent cells of the subject invention may be frozen so as to provide for prolonged storage.

2 Claims, No Drawings

HIGHLY TRANSFORMABLE BACTERIAL CELLS AND METHODS FOR PRODUCING THE SAME This application is a continuation of U.S. patent application Ser. No. 08/846,996, filed May 1, 1997. U.S. patent application Ser. No. 08/846,996 is incorporated herein by reference for any purpose.

1.0. TECHNICAL FIELD OF THE INVENTION

The present invention generally relates to the field of recombinant DNA technology. More specifically, the invention describes a novel bacterial mutation characterized by an ability to confer a high efficiency of transformation phenotype, and methods for producing highly competent cells using bacteria comprising the novel mutation.

2.0. BACKGROUND OF THE INVENTION

The process of introducing DNA (and other similar polynucleotides) into host cells is a key aspect of recombinant DNA technology. The process by which polynucleotides are introduced into host cells is called transformation. Bacterial cells generally remain the preferred hosts for the majority of recombinant DNA experiments and genetic engineering manipulations. Of particular interest for genetic engineering experiments is the bacteria *Escherichia coli*. Given that "competence" (the ability to efficiently uptake exogenous DNA) is not a natural feature of the *E. coli* growth cycle, artificial procedures must be used to introduce exogenous polynucleotides into *E. coli*. Of particular interest, are a variety of competency inducing procedures that render bacteria, including *E. coli*, more permeable to exogenous nucleic acid. Bacterial cells that have been treated to enhance their permeability to polynucleotides are generally referred to as competent cells.

There are many established procedures for making competent cells. These procedures include the $CaCl_2$ incubation methods of Mandel and Higa, *J. of Mol. Biol.* 53:159 (1970), as well as numerous well-known variants thereof. Hanahan has made a detailed study of factors that effect the efficiency of transformation of *E. coli* cells (*J. Mol. Biol.* 166:557–580 (1983)) where he describes a method of producing highly competent *E. coli* cells comprising the step of washing *E. coli* cells in a buffer comprising potassium acetate, KCl, $MnCl_2$, $CaCl_2$, and hexamine cobalt chloride, which is generally regarded as the best available method of producing highly competent *E. coli*. Another method of producing competent *E. coli* cells is described by Jessee et al., U.S. Pat. No. 4,981,797. Jessee et al. shows that high levels of competency may be induced by growing *E. coli* cells in a temperature range of 18° C. to 32° C. as part of the competency inducing procedure.

The various techniques for rendering *E. coli* cells competent produce competent *E. coli* cells having varying of transformation efficiencies. The precise mechanism by which DNA enters competent *E. coli* is not completely understood. Nor is it completely understood why one composition of competent *E. coli* cells differs in transformation efficiency from that of another composition of competent *E. coli* cells. Hanahan, in *Escherichia Coli and Salmonella Typhimurium: Cellular and Molecular Biology*, editor F. C. Neidhardt, American Society for Microbiology, Washington, D.C. (1987).

The above methods have been further optimized to achieve efficiencies of approximately $1 \times 10^9$ cfu/µg supercoiled plasmid DNA. Although this number appears high, the theoretical efficiency for the test plasmid (pUC) is $3 \times 10^{11}$ cfu/µg. Furthermore, when applied to practical laboratory conditions, such as the transformation of DNA substrates that were ligated rather than supercoiled, the actual number of colony forming units observed was many orders of magnitude lower than that achieved when supercoiled pUC was used as a test substrate.

Even with past developments, only a minute fraction of the cells in a preparation of "competent" *E. coli* cells, are actually competent for DNA uptake. Thus, the methods and cells presently used to generate compositions of competent *E. coli* cells may yet be significantly improved.

Alternatively, other methods of producing competent cells may result in the formation of competent *E. coli* cells that each have an enhanced ability to replicate and expresses exogenously added DNA. Hanahan, in *J. Mol. Bio.* 166: 557–580 (1983) has speculated that competent *E. coli* cells contain channels for transport of DNA across the cell envelope, and that the limiting step in determining the competency for transformation of *E. coli* cells are events that occur in the cell after the cell has taken up the DNA of interest, i.e., the establishment step. Another factor affecting the transformation efficiency of a composition of competent *E. coli* cells is the genotype of the cells. Some strains of *E. coli* are known to produce more highly transformable competent cell compositions than other strains of *E. coli* that have been subjected to the same competency inducing procedure.

Subsequent to the initial discovery that *E. coli* could be rendered competent for DNA uptake, studies have been undertaken to increase transformation efficiency. The maximum level of transformation efficiency obtained using the method of Hanahan described in *J. Mol. Bio.* 166:557–580 (1987), which employs the step of washing cells in a buffer comprising potassium acetate, KCl, $MnCl_2$, $CaCl_2$, glycerol, and hexamine cobalt chloride, is approximately $1 \times 10^9$ transformants per microgram of supercoiled pUC18 plasmid DNA. On a per cell basis, this translates to approximately 1 cell out of 300 in the population actually becoming transformed. However, the above number generally only applies to small supercoiled plasmids. When large plasmids, or ligated molecules are involved, as is the case with many recombinant DNA experiments, the number of "competant" cells that actually become transformed is dramatically reduced. As such, a need continues to exist for new and improved methods for producing competent *E. coli* of superior transformability, as well as new strains of *E. coli* that demonstrate superior transformability. Such methods and strains would be of wide interest to most researchers in the field of genetic engineering in that the number of transformations required to obtain the desired result would be minimized. Thus, for example, larger genetic libraries could be built more easily as well as the construction of complex recombinant molecules achieved more readily.

3.0. SUMMARY OF THE INVENTION

The invention described herein provides a method of producing novel strains of highly transformable gram negative bacterial cells such as *E. coli* that may be used in a wide variety of competency inducing procedures. The methods of the subject invention involve methods of mutagenizing bacterial cells, selecting the mutagenized cells for a high efficiency transformation phenotype, and using the mutated genetic material responsible for (or associated with) high efficiency transformation to construct novel compositions of highly competent bacteria.

One embodiment of the present invention is a biologically pure strain of E. coli which is characterized as comprising an Hte mutation that confers a high efficiency of transformation (of foreign plasmids) phenotype relative to E. coli that lack an Hte mutation.

Another embodiment of the subject invention is the novel strain of E. coli XL10-GOLD, having the genotype Δ(mcrA) 183Δ(mcrCB-hsdSMR-mrr)173endA1 supE44 thi-1 recA1 gyrA96 relA1 lac tet$^R$ Hte[F'proAB lacI$^q$ZΔM15 Tn10(Tet$^R$) Amy Cam$^R$]. The invention further relates to frozen compositions of such cells, and methods for making the cells competent.

An additional embodiment of the present invention is the use of cells harboring an Hte mutation to clone or subclone heterologous genetic material of interest.

4.0. DETAILED DESCRIPTION OF THE INVENTION

The presently described invention includes gram negative bacterial cells, such as E. coli, that have been genetically modified to have enhanced transformation efficiency after being processed by an appropriate competency inducing procedure when compared to E. coli cells lacking the genetic modification. It has previously been shown that microorganisms bearing the proper genotype can display drastically enhanced transformation efficiency. In particular, U.S. Pat. No. 5,512,468, herein incorporated by reference, describes how the presence of the α-amylase gene in E. coli increases transformation efficiency.

The bacterial cells of the subject invention have been modified by the incorporation of a mutated Hte region. For the purposes of the present invention, the Hte region is characterized as a region which confers a high efficiency of transformation phenotype to cells harboring mutated forms of the Hte region. For the purposes of the present disclosure, the term "incorporation" as used herein shall mean the insertion of a mutated variant of the Hte region into the bacterial genome by homologous or nonhomolgous recombination, or the episomal presence of a mutant variant of the Hte region. Similarly, an Hte mutant is defined as a mutated form of the Hte locus that confers a high efficiency of transformation phenotype to a bacterial host harboring the Hte mutation.

Preferably, bacterial hosts harboring mutated variants of the Hte region shall be biologically pure. For the purposes of the present invention, a "biologically pure" strain of bacteria shall be derived from a single cell, or shall be at least about 99.9 percent comprised of cells of directly common ancestry.

The Hte region was identified by screening/selecting mutagenized E. coli for an enhanced transformation efficiency phenotype. In particular, a series of transformation steps were used to screen mixed populations of bacterial mutants to selectively enrich the population of "competent" cells. The selective feature of the transformation screening method stemmed from the use of a limiting amount of DNA. Limiting the amount of DNA used during transformation unexpectedly allowed for the enrichment and identification of cells having an increased transformation efficiency after antibiotic selection was applied. Previous studies had indicated that essentially all of the cells in a given culture bind exogenously added DNA, but only the small fraction of cells that are actually "competent" for DNA uptake are transformed. Given these reaction kinetics, one would not expect that limiting the amount of DNA added would allow for the efficient selection for cells bearing enhanced transformation efficiency. Generally, a "limiting" amount of DNA describes a situation where the molar ratio of DNA/cells is less than 1, typically less than about 0.5, more typically less than about 0.1, and specifically less than about 0.05, and preferably about 0.001.

Multiple rounds (at least two rounds up to any practical number) of selection by transformation may be employed to more stringently select for cells having the property of being capable of high efficiency transformation. Preferably, succeeding rounds of selection by transformation will proceed using a series of different vectors and selectable markers. Where applicable, the different vectors used during the multiple rounds of selection by transformation shall preferably and respectively comprise origins of replication drawn from different plasmid incompatibility groups. Additionally, although it is not necessary, the various transformants obtained after a given round of selection may be individually or collectively recovered prior to the next round of selection by transformation.

After bacteria displaying the desired high efficiency of transformation phenotype were identified, a transposon library was generated, and generalized P1 transduction was used to move the mutated Hte region into suitable recipient strains. The resulting "Hte$^-$" bacteria displayed enhanced transformation efficiency relative to cells that did not incorporate the Hte region, and a particularly enhanced transformation efficiency for relaxed plasmids and large plasmids. For the purposes of the present invention, the term "transformation efficiency" refers to a measure of the competence level of a given composition of competent cells. Transformation efficiency is expressed in terms of the number of transformants obtained for each microgram (or other quantity) of exogenous DNA added to a competent cell composition.

Typically, the presence of the Hte region will functionally increase the transformation efficiency of a given bacteria by at least about two fold, more typically at least about four fold, and preferably by at least about one order of magnitude. Of particular interest is that the presence of the Hte region enhances the transformation efficiencies of large plasmids and topologically relaxed plasmids (plasmids that are neither substantially supercoiled nor underwound). For the purposes of the present invention, the term "large plasmid" shall typically refer to plasmids at least about 15 kb in size, preferably at least about 25 kb up to about 100 kb. For the purposes of the present invention, the presence of a mutant variant of the Hte region in a given bacteria will typically increase the transformation efficiency for large and/or relaxed plasmids of by at least about two fold, more typically at least about four fold, preferably by at least about six to eight fold, and more preferably by at least about one to two orders of magnitude.

A specific embodiment of the subject invention is the novel strain of E. coil XL10-GOLD. On Apr. 28, 1997, strain XL10-GOLD was deposited at the American Type Culture Collection (ATCC), Rockville, Md., USA, now located at Manassas. Va. USA under the terms of the Budapest Treaty on the International Recognition of the Deposit of Microorganisms for the Purposes of Patent Procedure and Regulations thereunder (Budapest Treaty), and is thus maintained and made available according to the terms of the Budapest Treaty. Availability of such strain is not to be construed as a license to practice the invention in contravention of the rights granted under the authority of any government in accordance with its patent laws.

The deposited culture has been assigned the indicated ATCC deposit number:

| | ATCC No. |
|---|---|
| XL10-GOLD | 55962 |

Other aspects of the invention include methods for rendering gram negative bacteria, such as *E. coli* cells competent for transformation. These methods minimally involve the step of transferring a polynucleotide encoding a suitably mutated variant of Hte region into *E. coli*. Such modified cells may subsequently be rendered competent using any of a wide variety of competency inducing procedures. For the purposes of the present invention, the term "competency inducing procedure" refers to any procedure used to render *E. coli* cells competent to transformation by exogenous DNA. Competency inducing procedures for *E. coli* (and other gram negative bacteria) are well known to the person of average skill in the art of molecular biology. Although competency inducing techniques vary considerably from one another, almost all competency inducing techniques involve the exposure of the cell to multivalent cations and near 0° C. Competency inducing techniques for use in the subject invention include, but are not limited to, the $CaCl_2$ incubation method of Mandel and Higa (*J. Mol. Bio.*, 53:159 (1970)), and the method of Hanahan, *J. Mol. Bio.*, 166: 557–580 (1983) which employs treating the cells in a series of buffers comprising potassium acetate, KCl, $MnCl_2$, $CaCl_2$, glycerol, and hexamine cobalt chloride. The method of Hanahan is particularly preferred for use in the subject invention. In addition to or in lieu of the buffers taught by Hanahan, buffers comprising rubidium chloride may also be used. Additional teaching may be found in, among other places, U.S. Pat. No. 4,981,797 (Jessee) and Sambrook et al., *Molecular Cloning: a Laboratory Manual*, 2nd Edition, Cold Spring Harbor Press (1989), and periodic updates thereof, and Hanahan and Bloom, in *Escherichia Coli and Salmonella Typhimurium: Cellular and Molecular Biology*, "Mechanisms of DNA Transformation", editor F. C. Neidhardt, American Society for Microbiology, Washington, D.C. (1996) which are herein incorporated by reference.

The competent cells of the subject invention may be transformed using most well known transformation procedures. These procedures typically involve the step of exposing competent cells to a heat pulse in the presence of exogenous DNA. Examples of such transformation procedures can be found in Mandel and Higa, *J. of Mol. Biol.* 53:159 (1970) and the standard high competency induction method described by Hanahan (1983) *J. Mol. Bio.* 166: 557–580 (1983).

The genetic constructs used to introduce the Hte region into a bacterial host may be designed to either replicate autonomously in the bacterial cell or to be incorporated into the genome of the bacterial cell. Preferably, genetic constructs encoding the Hte region are designed to provide for the stable maintenance of the Hte region within the host cell. Additionally, where the genetic construct replicates autonomously, the construct should not comprise an origin of replication, e.g. a colE1 replicon, that results in plasmid incompatibility with widely used bacterial vectors.

In addition to polynucleotide sequence encoding the Hte region, the genetic construct may also comprise any one of a number of conventional genetic vectors such as plasmids, phages, phagemids, and the like.

Preferably, the genetic constructs will express the essential genes encoded within the Hte region. Methods for expressing genes of interest in *E. coli* and other gram negative bacteria are well known. For examples of such methods see *Gene Expression Technology: Methods and Enzymology*, Vol. 185, Goeddel, Editor, Academic Press, Incorporated, San Diego, Calif. (1991).

Genetic constructs containing polynucleotides encoding the Hte region may be introduced into *E. coli* cell using any of a wide variety of transformation techniques including transformation, conjugation, triparental mating, specialized or generalized phage transduction, electroporation, and the like. The competent *E. coli* cells of the subject invention are produced when the described Hte cells are subject to a competency inducing procedure. After the *E. coli* cells have been rendered competent by a competency inducing procedure, the cells may be frozen so as to retain their competence upon thawing. Frozen competent cells are a particularly useful embodiment of the invention because they may be stored for prolonged periods of time, thus avoiding the need to constantly produce fresh preparations of competent cells. Protocols for preparing frozen competent cells are known to the person of average skill in the art. An example of such a protocol can be found in Hanahan, *J. Mol. Bio.* 166:557–580 (1983).

It is also to be appreciated that the measured transformation efficiency of a given composition of competent cells using a given transformation protocol will generally vary depending upon the particular exogenous DNA used to transform the bacteria. In particular, factors such as the size and topology of the exogenous DNA may significantly affect transformation efficiency.

The introduction of a genetic construct encoding the Hte region increases the transformation efficiency of compositions of a wide variety of *E. coli* strains. Typically, the genotype of a given strain of *E. coli* containing the Hte region, may be selected to be particularly useful for a given genetic engineering experiment.

Given the presently described selection process, phenotypic screening methods, and the deposited strains of *E. coli*, a variety of genetic and molecular biological methods may be employed to further define the structure of the Hte region and the specific mutation or mutations responsible for the high efficiency transformation phenotype. Examples of such methods have been described in Maniatis, T. et al., *Molecular Cloning*, (1st Ed.) and Sambrook, J. et al., (2nd Ed.), Cold Spring Harbor Laboratory, Cold Spring Harbor (1982, 1989); *Methods in Enzymol.*, Vols. 68, 100, 101, 118 and 152–155 (1979, 1983, 1986 and 1987); and *Molecular Cloning*, D. M. Clover, Ed., IRL Press, Oxford (1985). Medium compositions and general microbial genetic techniques have been described in Miller, J. H., *Experiments in Molecular Genetics*, Cold Spring Harbor Laboratory, New York (1972), and Miller, J. H., *A Short Course in Bacterial Genetics*, Cold Spring Harbor Press, New York (1995), herein incorporated by reference, as well as the references previously identified. DNA manipulations and enzyme treatments are carried out in accordance with manufacturers' recommended procedures.

Once the specific gene or genes (in the case of an operon) in the Hte region that are responsible for the high efficiency transformation phenotype are characterized, the encoded products that are associated with the high efficiency transformation phenotype may also be characterized. Accordingly, an additional embodiment of the present invention are Hte proteins, or functional derivatives thereof, that are associated with the high efficiency transformation phenotype as identified by the presently described selection methods and screening methods.

The term "Hte protein" as used herein refers not only to proteins having the amino acid residue sequence of the mutated form of the Hte protein that provides the desired phenotype, but also refers to functional derivatives and variants of naturally occurring Hte protein.

A "functional derivative" of a Hte protein is a compound having a qualitative biological activity in common with Hte protein. Preferably, "functional derivatives" include, but are not limited to, fragments of mutant or native Hte proteins and derivatives of Hte proteins and their fragments, provided that they are associated with conferring the desired phenotype. "Fragments" comprise regions within the sequence of a mature polypeptide. The term "derivative" is used to define amino acid sequence variants of a Hte protein, and the term "variant" also refers to amino acid sequence and variants within this definition.

Preferably, the functional derivatives are polypeptides which have at least about 65% amino acid sequence identity, more preferably about 75t amino acid sequence identify, even more preferably at least 85% amino acid sequence identity, most preferably at least about 95% amino acid sequence identity with the corresponding region of a corresponding Hte protein or polypeptide. Most preferably, the functional derivatives of a Hte protein retain or mimic the region or regions within the Hte protein that are directly responsible for conferring the high transformation efficiency phenotype.

Functional derivatives of Hte protein also include chemically modified or derivatized molecules derived from Hte protein.

The phrase "functional derivative" further and specifically includes peptides and small organic molecules having a qualitative biological activity in common with Hte protein.

"Identity" or "homology" with respect to a Hte protein is defined herein as the percentage of amino acid residues in the candidate sequence that are identical to the corresponding residues of a native Hte polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

Once a gene encoding a Hte protein, or functional derivative thereof, has been identified and cloned, amino acid sequence variants of Hte protein, or functional fragments thereof, are prepared by methods known in the art by introducing appropriate nucleotide changes into a native Hte DNA sequence, or by in vitro synthesis of the desired polypeptide. There are two principal variables in the construction of amino acid sequence variants: the location of the mutation site and the nature of the mutation. The amino acid sequence variants of Hte protein are preferably constructed by mutating the Hte gene to generate corresponding Hte amino acid sequence variants that do not occur in nature.

Such mutants may be engineered, for example, as frameshift mutations that result in an altered reading frame and early termination of translation to produce a truncated Hte molecule. Similarly, in-frame deletions may be made in the Hte gene that effectively result in the removal of discrete portions of the Hte protein. Such amino acid sequence deletions generally range from about 1 to 30 residues, more preferably about 1 to 10 residues, and are typically, but not necessarily, contiguous. Deletions are generally introduced in regions that are not directly involved in ligand binding.

Alternatively or in addition, amino acid alterations can be made at sites that differ in Hte proteins obtained from other bacterial species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" Cunningham and Wells, *Science* 244, 1081–1085 (1989). Here, a residue or group of target resides is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding a Hte protein variant can, for example, be obtained by chemical synthesis.

More preferably, DNA encoding a Hte protein amino acid sequence variant is prepared by site-directed mutagenesis of DNA that encodes an earlier prepared variant or a nonvariant version of the Hte protein. Site-directed (site-specific) mutagenesis allows for the production of Hte protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 50 nucleotides in length is preferred, with at least about 5 to 10 residues on both sides of the junction of the sequence being altered. In general, the techniques of site-specific mutagenesis are well known in the art, as exemplified by publications such as, Edelman et al., *DNA* 2:183 (1983). As will be appreciated, the site-specific mutagenesis technique typically employs a phage vector that exists in both a single-stranded and double-stranded form. Typical vectors useful in site-directed mutagenesis include vectors such as the M13 phage. This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500, 1982. Also, plasmid vectors that contain a single-stranded phage origin of replication, Veira et al., *Meth. Enzymol.* 153:3 (1987) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis may be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desires mutation. This heteroduplex vector is then used to transform appropriate host cells such as HB101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of Hte protein. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primer can be easily sequenced. PCR amplification using a primer pair like the one just described results in a population of DNA fragments that differ at the position of the mutation specified by the primer, and possibly at other positions, as template copying is somewhat error-prone.

Further details of the foregoing and similar mutagenesis techniques are found in general textbooks, such as, for example, Sambrook et al., *Molecular Cloning: H Laboratory Manual 2nd edition*, Cold Spring Harbor Press, Cold Spring Harbor (1989), and *Current Protocols in Molecular Biology*, Ausubel et al. eds., John Wiley and Sons (1995).

Naturally-occurring amino acids may be divided into groups based on common side chain properties:
(1) hydrophobic: norleucine, met, ala, val, leu, ile;
(2) neutral hydrophobic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another (see generally Orcutt, B. C. and Dayhoff, M. O., Scoring Matrices, PIN Report MAT-0285, February 1985). Variants obtained by non-conservative substitutions are expected to result in significant changes in the biological properties/function of the obtained variant, and may result in Hte protein variants that block normal Hte function. Amino acid positions that are conserved among various species are generally substituted in a relatively conservative manner if the goal is to retain biological function.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the Hte coding region) may range generally from about 1 to 10 residues, more preferably 1 to 5 residues, more preferably 1 to 3 residues. Examples of terminal insertions include variant Hte proteins that fuse a heterologous N-terminal signal sequence to the N-terminus of the Hte protein to provide for directed cellular localization or secretion of the Hte protein from recombinant host cells. Such signal sequences will generally be obtained from, and thus homologous to, the intended host cell species. Suitable sequences include STII or Ipp for *E. coli*. Other insertional variants of the Hte protein include C-terminal fusions. Additionally, further variants of the Hte protein may by obtained via chemical modification of the constituent amino acids, or the incorporation of unnatural amino acids or amino acids of nonbiological origin.

Since it is often difficult to predict in advance the characteristics of a particular variant Hte protein, it will be appreciated that screening will be needed to select the optimum variant. For this purpose genetic screening assays, such as those described hereinbelow, will prove invaluable.

Given that altered transformation efficiency has been associated with altered cell envelopes (e.g., altered LPS in the outer membrane, and altered membrane fluidity), it is also possible that the desired phenotype provided by the Hte region is related to a structural anomaly caused by a disabled or functionally inactive cellular protein. For example, mutagenesis of the Hte gene may have resulted in generation of a stop codon in a key coding region by one or more transition or transversion mutations. Additionally, a frame-shift mutation may have disrupted a native open reading frame to produce the desired high efficiency transformation phenotype. Where such a mutation is involved, a particularly preferred method of generating the desired phenotype is to delete all or a substantial portion of the mutated gene. Optimally, at least an essential portion of the Hte gene will be deleted, or a suitable frame-shift mutation may be generated by deleting a number of bases not divisible by the number three. By deleting the mutated gene, the chances of reversion are dramatically reduced.

Optionally, the Hte gene may be inactivated by insertional mutagenesis by inserting a selectable marker into or near the Hte coding region. Accordingly, the stable maintenance of the Hte mutation may be ensured by providing the proper antibiotic selection techniques. Inactivation of the Hte locus by deletion or insertional activation is also preferred where the Hte gene encodes a repressor or activator molecule for a gene or operon where the resulting constitutive expression (or inactivation) of the gene or operon contributes to the Hte phenotype.

It is also possible that the presently described Hte mutation results in the enhanced expression or over expression of a gene product or operon. Conversely, it is also possible that mutating the Hte region results in the under expression of a particular gene product or operon.

Additional embodiments of the present invention are compounds that inhibit or enhance the normal function of Hte protein such that the microorganisms that express or have been exposed to or treated with such compounds exhibit enhanced transformation efficiency, or the Hte phenotype.

The presently described $Hte^-$ competent cells may also be combined with other desired genetic markers. For example, the relevant $Hte^-$ region may be moved into a bacteria engineered to contain and express a gene encoding a carbohydrate degrading enzyme or a functional derivative thereof. Preferably, the carbohydrate degrading enzyme is capable of degrading starch. The expressed enzyme is preferably located in the periplasmic space of the cell; however, the practice of the invention is not dependent upon any particular theory as to the cellular location of expressed carbohydrate degrading enzymes.

Additionally, the Hte region may be used in conjunction with cloning vectors that may be screened using LacZα fragment complementation in conjunction with a particular mutation within the LacZ gene. Similarly, the cell may contain various other deletions or mutations in order to provide for complementation by the transforming DNA. The host cell may either possess or lack a restriction-modification system in order to expedite cloning. The host cells may also lack one or more recombination systems, e.g., RecA, RecBC. Particularly preferred strains of *E. coli* for use in the invention are the XL1-Blue™ strain (Stratagene, La Jolla, Calif.), the XL1-Blue MR strain, and the SURE™ strain (Stratagene, La Jolla, Calif.) that have been modified by the addition of a genetic construction for the expression of alpha-amylase isolated from a thermophilic bacteria and have the ATCC accession numbers 69480, 69481 and 69482, respectively. The plasmid containing the alpha-amylase gene in the *E. coli* strains having ATCC accession numbers 69480, 69481 and 69482 may be readily transferred to other strains of bacteria using techniques well known to the person of average skill in the art. Similarly, the person of average skill in the art may excise the alpha amylase gene from plasmids in the *E. coli* strains having accession numbers 69480, 69481 and 69482 and transfer the alpha amylase gene to a new genetic construct prior to transferring the gene to a new strain of bacteria.

While reference is made to *E. coli*, other gram negative bacteria cells may also be rendered more competent by the introduction of the Hte region. For example, bacteria from the Genera *Pseudomonas, Rhizobium, Agrobacterium, Salmonella; Proteus, Shigella, Klebsiella* and the like.

Although specific examples of mutagenic techniques have been described herein, one skilled in the relevant art is deemed capable of practicing any of a wide variety mutagenic techniques to practice the invention described in the present disclosure.

Given the enhanced transformation efficiency of Hte mutants, the presently described cells are particularly useful for the cloning and subcloning of heterologous genetic material of interest. Typically, such genetic material includes procaryotic genes of interest, or animal, and particularly mammalian, genes or cDNA. Optionally, the genetic material of interest will exist in a genomic or cDNA library. Additionally, given the enhanced transformation efficiency of large plasmids, Hte mutants are also particularly useful in the cloning, subcloning, and engineering of genetic material of interest involving large plasmids such as yeast shuttle vectors, mammalian virus vectors (retrovirus, adenovirus, papilloma virus, herpes virus, adeno-associated virus, rabies virus, and the like. See generally, Sambrook et al., *Molecular Cloning*, Cold Spring Harbor Laboratory Press, Cold Spring Harbor, N.Y., Vol. 3:16.1–16.89 (1989)), plant virus vectors, or insect vectors (e.g., bacculo virus).

The invention having been described above, may be better understood by reference to the following examples. These examples are offered solely for the purpose of illustrating the subject invention, and should not be interpreted as limiting the invention in any way whatsoever.

5.0. EXAMPLES

5.1. Mutagenesis of the *E. coli* Chromosome

Mutagenesis of the *E. coli* chromosome was performed by standard procedures adapted from Miller, J., (1995), A short Course in Bacterial Genetics. Cold Spring Harbor Press, Cold Spring Harbor, N.Y. A 50 ml logarithmically growing culture of *E. coli* strain CAG1001 (from C. Gross, U. Wisconsin) was pelleted at 4000 rpm in a Sorvall centrifuge, washed once with MC buffer (100 mM $MgSO_4$, 5 mM $CaCl_2$ and suspended in 40 ml of MC. 5 ml was aliquotted to each of 6 sterile Petri dishes. Five of these samples were treated with ultraviolet light of varying intensities in the Stratagene Stratalinker 2400 (Catalog #400075) as follows. The cover of the dish was removed and laid alongside the cells and exposed to either 100 uJ, 200 uJ, 300 uJ, 400 uJ, or 600 uJ; the sixth sample was not treated. Prior to exposure, 5 µl of each aliquot was removed, diluted $10^{-4}$, and 100 µl were plated on an LB plate to determine cell viability. After exposure, the cells were pipetted back into a 50 ml conical test tube and 1.2 ml of 5× LB added. The mutagenized (and control) samples were incubated for 1 hour and 5 µl were removed for viability plating. 100 µl of $10^2$, $10^{-3}$, and $10^{-4}$ dilutions were then plated on LB plates while the culture was permitted to grow overnight.

The following morning, the number of colonies on each late were determined and compared to their nonmutagenized counterparts. UV intensities that resulted in 95%–99% cell death were selected as being appropriate; the overnight cultures corresponding to these samples were pooled, DMSO to 8% final concentration added, and the cells were stored at −80° C.

In order to retrieve an *E. coli* mutant that exhibited an increased transformation efficiency for both large and small plasmid molecules, the U.V. survivors described above were pooled, grown to mid-logarithmic phase, and competent cells were prepared by standard procedures. These cells were then transformed with a limiting amount of pUC DNA (1 pg) and ampicillin resistant transformants selected. The rationale for this screening was that if fewer DNA molecules than cells were added to the transformation, any specific cell that was more "transformable" would have a higher likelihood of incorporating the pUC DNA molecule. *E. coli* CAG1001 was use as a starting strain was because it carried no known mutations and was supO (no known suppressor tRNA activity). In addition, it transformed poorly when compared with strains like XL1-Blue/DH5α (unpublished observations). Therefore, since the background transformation efficiency was lower, any mutant possessing the desired characteristic might be more apparent. From this experiment, 1,500 transformants were obtained from each pool. It was presumed that among these cells would be mutants that had a higher transformation efficiency (along with the majority that were unchanged but transformed by statistical probability). These transformants were then pooled, grown to mid-logarithmic phase, and competent cells were again prepared. These pools were then transformed with 1 ng of pQL1, a pACYC 184 derivative (Quinn Lu, unpublished) that can be stably maintained along with pUC, and carries a different antibiotic selectable marker (chloramphenicol). Plates with about 200 transformants were selected and saved. As a method for enriching the number of mutants of interest, the number of transformants/pool was reduced. By using this number, it was recognized that each pool may contain as few as a single mutant that actually had an enriched transformation phenotype. Analysis of these 200 colonies was then conducted by randomly choosing 90 of the colonies and preparing small-scale preparations of competent cells. The 90 were transformed with pAL205, a RSF1010 derivative that is relatively large (15 kb), tetracycline resistant, and whose origin of replication is compatible with those of pUC and pACYC184. Of these 90, the 15 that provided the greatest number of transformants (actual efficiencies were not determined since the cell density and other factors normally controlled for were not because so many were analyzed concurrently) were chosen for further analysis.

Competent cells from these 15 strains were then prepared by the standard procedure with monitoring of optical density and various other parameters. Four of the strains exhibited a significant increase in transformation efficiency and these four represented the next pool for mutant retrieval (numbers 7, 12, 33, and 59).

5.2. Preparation of Competent Cells for Enrichment and Evaluation

Competent cells of either pools of potential mutants or isolated mutants (see below) were prepared identically. The appropriate volume of cells (10 ml–250 ml, depending on experiment) were grown in LB media to an optical density (O.D.$_{600}$) of approximately 0.35. The cells were transferred to the appropriate centrifuge tube (for the 10 ml cultures that were grown in a 50 ml conical test tube, no transfer was necessary) and pelleted at 1,400 rpm at 4° C. The pellet was suspended in one half of its initial volume in FSB (10 mM potassium acetate pH 7.6, 45 mM manganese chloride, 10 mM calcium chloride, 3 mM hexamine cobalt chloride, and 8 percent glycerol) and centrifuged as before. The cells were then suspended in 1/20 the original volume of FSB, DMSO was added to a final concentration of 8%, and the competent cell preparation was frozen at −80° C. When small volume competent cell preparations were made for immediate evaluation, the DMSO addition and freezing steps were bypassed and 100 µl of the cell suspension tested immediately.

Transformation of competent cells was done using standard conditions (see Stratagene Competent Cell Manual for details). β-mercaptoethanol or UltraBeta, as described in these manuals, was either added or withheld, depending on the application (See text for details).

5.3. λ::Tn10 Mutagenesis

Random insertion of the transposon Tn10 (tetracycline resistance) was performed as described by Kleckner et al., 1991, Methods in Enzymology 204:139. λ:1098 (Tn10) is a defective λ virus that is unable to replicate in or lysogenize a supO E. coli host due to amber mutations present in the λ O gene (DNA replication) and int gene (lysogenization). Thus, upon entry into a supO E. coli, these phage are incapable of further propagation, but remain capable of expressing the encoded genes. This phage carries a segment of DNA encoding the Tn10 tetracycline resistance gene (surrounded by the IS10 elements required for transposition). The phage also carries the Tn10 transposase protein that is required to catalyze random transposition. When supO E. coli are infected with λ:1098, tetracycline resistant bacteria can be selected that contain a copy of the tet resistance gene located somewhere on the chromosome. (Note: The stock of λ:1098 can be prepared on a supE E. coli since suppression of the amber mutations in the λ genes will permit replication and subsequent lysis of this host.

The λ:1098 insertions are generated by infection of 100 µl of logarithmically growing E. coli with $10^8$ phage particles; since the transposition frequency is $10^{-4}$ to $10^{-5}$, approximately $10^3$–$10^4$ tetracycline resistant colonies can be obtained using this system. When a greater number of random Tn10 insertions were desired, multiple infections were carried out.

The 4 potential mutants described in section 5.1. above were in a CAG kan$^R$ prototrophic background. Therefore, it was necessary to "transfer" all chromosomal segments from these four to an appropriate derivative of XL2-Blue (XL1-MRA) where screening could be repeated. The random transposition mapping scheme was used to introduce the tet resistance gene randomly throughout the E. coli chromosome. The random transposition method required that the cells be non-suppressing (sup$^o$) and tetracycline sensitive.

Each of the four potential mutants were subjected to the random transposition of the tetracycline resistance gene, and approximately 5,000 colonies were collected. If transposition were random, 50 insertions would statistically represent 1 insertion/100 kilobase pairs on the E. coli genome (the reason for using the 1 insertion/100 kb will be explained below). However, we selected approximately 5,000 Tet$^R$ derivatives to ensure that all regions of the pool were represented and could be retrieved during generalized transduction.

5.4. Preparation of P1 Lysates

P1 phage lysates were prepared as described in Miller (1995). A 5 ml culture of the strain of interest was grown to mid-log phase at 37° C. in LB supplemented with 5 mM CaCl$_2$. 1 ml of cells were pipetted into a 12 ml Falcon 2059 tube and 1 µl of high titer P1 stock ($10^8$–$10^9$ pfu/ml; prepared on JM101) added. For most stocks, infections were done in quadruplicate and combined. The phage and cells were incubated at 37° C. for 15–20 minutes without shaking. The lysate was then plated by adding 2.5 ml of top agar (supplemented with CaCl$_2$ to 5 mM) to the sample poured onto an NY plate and incubated at 37° C. overnight. The following morning, the top agar was scraped into a 12 ml centrifuge tube. The plates were washed with 1 ml of LB and the remaining agar/slurry added to the tube. 5 drops (dispensed with a pasteur pipette) of chloroform were then added to the tube and suspension was vortexed (10–20 seconds on highest setting). The samples were incubated at room temperature for minutes, then centrifuged at 5,000 rpm in a Sorvall centrifuge (4° C.) for 15 minutes. The phage containing supernatant was recovered and transferred to a new 12 ml centrifuge tube, capped tightly, and stored at 4° C.

5.5. P1 Transduction

P1 transduction was performed as described by Miller (1995). 5 ml of the recipient strain was grown overnight in LB media supplemented with 5 mM CaCl$_2$. The stationary culture was harvested by centrifugation in a Sorvall Centrifuge at 5,000 rpm for 5 minutes and suspended in an equal volume of MC buffer (100 mM MgSO$_4$, 5 mM CaCl$_2$). The cells were placed back into a 37° C. air shaker and incubated for 20 minutes, then centrifuged as before. The pellets were suspended in 500 µl volume MC buffer; 100 µl of the cell suspension was the transferred to a 12 ml Falcon centrifuge tube. 1 to 100 µl of the P1 lysate (the amount varied depending on the individual titer; accordingly, for each transduction 1, 5, 25, and 100 µl were tested) was added to each tube. One sample was always left untreated as a control. The P1 infected cells were incubated at 37° C. for about 15–20 minutes. The reaction was terminated by the addition of 200 µl of 1 M sodium citrate. 0.5 ml of LB was added to each sample and cells were grown at 37° C. for one hour to allow expression of the drug resistance gene (tetracycline resistance in the experiments described here). After expression, the entire contents of the tube plated on LB or NZY plates with the appropriate antibiotic.

Retrieval of the tetracycline resistance genes (and thus, random regions of the four E. coli genomes discussed in section 5.3. was accomplished by P1 transduction. P1 is a bacteriophage that upon infection of a sensitive E. coli strain, replicates its DNA, packages it, eventually causes host cell lysis and death. 99% of all packaged particles are infective P1 particles, and 1% are random 100 kb pieces of host cell DNA (i.e., *E. coli* chromosomal DNA) that are packaged in error. When these lysates are used to infect a new host; 99% of these new cells are infected and killed and 1% become recipients for 100 kb segments of *E. coli* genomic DNA from the previous strain. If the lysate was prepared on an *E. coli* strain that has an integrated selectable marker (like the Tn10 tet resistance gene), and the recipient is capable of homologous recombination, then a chimeric *E. coli* strain can be generated that contains this 100 kb region from the P1-grown host in place of its own. In this manner, by pooling the 5,000 tet resistant colonies from the mutant pool and transferring them to a new strain (XL1-MRA, a recA$^+$, F$^-$ version of XL2-Blue), random chromosomal regions from the higher transforming pool were selected. Approximately 5,000 tet$^R$ transductants were selected for each of the four mutants, pooled, and subject to the transformation enrichment experiments described above. 1 ng of pACYC177 (kan$^R$) was used to transform each pool, and 300–500 transformants were subsequently pooled and transformed with 1 ng of pAL205 (Chloramphenicol resistant) and 50–150 colonies selected. These 50–150 colonies were then pooled and transformed with pUC, and 20–40 of the resulting colonies were again pooled. These three further rounds of enrichment were performed in order to screen for the Tet$^R$ transposons that lie adjacent to the mutation rather than Tet$^R$ transposons that integrated elsewhere. The 20–40 transformants were then infected with P1 and a new lysate was prepared that should contain the Tet$^R$ gene adjacent to a segment that provides for improved transformation efficiency.

These four P1 lysates were then transduced into XL1-Blue MR carrying pJC859. This plasmid is a pBR322 derivative harboring the *E. coli* recA$^+$ gene (necessary for P1 transduction to proceed) and individual transductants were streaked and analyzed for transformation efficiency compared with parental XL1-Blue containing pJC857 (Table 1).

From each of the four P1 pools identified, a single colony was chosen that exhibited an increase in transformation efficiency. These mutants were designated 7, 12, 33, and 59, to correspond to the original mutants isolated.

TABLE 1

COMPARISON OF THE TRANSFORMATION EFFICIENCIES OF POTENTIAL MUTANTS AND THE PARENTAL STRAIN

| HOST | NUMBER OF TRANSFORMANTS |
| --- | --- |
| #7 | 168 |
| #12 | 190 |
| #33 | 140 |
| #59 | 154 |
| XL1MR/pJC857 | 104 |

5.6. Transferring Potential Mutations into XL1-BLUE Background

XL1-MR/pJC859 is a F$^-$ derivative of XL1/XL2 blue that contains a plasmid expressing the *E. coli* RecA$^+$ gene product. In order to convert this strain to an isogenic version of XL2-Blue, it was necessary to remove the RecA plasmid from the cell. This was accomplished by an extended growth in LB Tet (no ampicillin selection) for 50–100 generations and screening single colonies for ampicillin sensitivity. At least one of each was identified for the four mutants; approximately 100–500 individual colonies were screened in order to isolate the ampicillin sensitive cell of interest.

Each of the four *E. coli* mutants were then used as recipients for F' conjugal mating with the F' amylase episome of XL2-Blue. Small scale competent cell preparations were then made on these exconjugants and transformation efficiencies using pUC and pRK2013 (a 25 kb plasmid) were determined (see Table 2). The strain that exhibited the highest relative efficiency with both pUC and pRK2013 (Mutant #12) was then used for large scale preparations.

TABLE 2

TRANSFORMATION WITH SMALL AND LARGE SUPERCOILED PLASMID DNA MOLECULES

| STRAIN | EFFICIENCY/ µg pUC | EFFICIENCY/ µg pRK2013 |
| --- | --- | --- |
| XL10-GOLD | $5 \times 10^9$ | $3.6 \times 10^4$ |
| XL2-Blue | $5 \times 10^9$ | $6.2 \times 10^3$ |
| SCS-1 | $1 \times 10^9$ | $7.6 \times 10^2$ |
| DH5α | $1 \times 10^9$ | $6.2 \times 10^2$ |

The transformation efficiencies shown in Table 2 were determined as follows. 100 pg pUC or 500 ng of pRK2013 were added to 100 µl of competent cells and transformed following the standard protocol. Aliquots (0.1%, 1%, 10%, etc.) of each transformation mix were then plated on the appropriate selection plates to evaluate the transformation efficiency. These data show that although the relative transformation efficiency for a small plasmid (pUC) remained unchanged compared with XL2-Blue, the efficiency of transformation with the 25 kb pRK2013 plasmid was dramatically increased in XL10-GOLD. The observed increase in the transformation efficiency of large plasmids is a particularly useful feature of cells harboring the Hte$^-$ mutation.

Subsequent transduction studies have shown that when the Hte$^-$ region from XL10-GOLD was transferred into a heterologous strain of *E. coli*, an approximately six-fold enhancement of transformation efficiency was observed. Given that P1 transduction may be used to transfer the Hte region between various hosts, the Hte region may be further characterized as located within that region of DNA that lies within 100 kb of the transposon encoded tet gene incorporated into XL10-GOLD.

5.7. Optimization of Transformation

The addition of certain compounds to competent cells 10 minutes prior to addition of DNA may dramatically improve transformation. For the cell line that performed best above, transformation efficiency was optimized by making matrices of the two compounds present in the current UltraBeta. Both pUC and pRK2013 were employed as substrates and the optimal concentration of each component was determined. Further examples of such optimization parameters include, inter alia, the use of a 110 mM NaCl solution, and 50 mM 2-mercaptoethanol.

5.8. Analysis of Other Features of Competent Cells

Other features of competent cells that are necessary to be present in any improved version are the ability to perform blue-white color screening (presence of F' lacIqZΔM15), the lack of known restriction systems (Hsd$^-$, McrBCF$^-$, McrA$^-$), and the lack of the EndA1 nuclease that is responsible for interfering with miniprep DNA isolations. These features were tested for the #12 mutant. The cells maintained all of these characteristics. Therefore, mutant 12 was used to pursue further experiments evaluating its utility for PCR cloning and library construction.

5.8.1. Efficiency with Ligated DNA

In general, ligated DNA transforms with significantly lower efficiency than that of supercoiled DNA. To evaluate this difference and to determine whether the mutant 12 variant was better able to transform ligated molecules as compared to existing strains of *E. coli* the following experiment was performed. Ten ng of pCAL n-EK plasmid DNA was prepared for ligation independent cloning (LIC, Stratagene catalog #214310) following the directions provided. A kanamycin resistance gene was PCR amplified using primers containing compatible LIC ends and the amplified product was treated as directed to produce the appropriate compatible ends. These DNAs were annealed following suggested conditions for LIC. An aliquot of the annealed DNA mixture was then used to transform mutant 12 (hereafter referred to as XL10-GOLD) AND DH5 from Life Technologies. The number of colony forming units (cfu) were compared with the number observed when supercoiled pUC DNA as the substrate. The data demonstrated that the number of cfu for the annealed (i.e., ligated) DNA was 20 fold greater for XL10-GOLD compared to DH5, and the pUC efficiency was 5 fold greater. This enhancement of transformation for ligated DNA molecules is a significant difference between these strains.

A second series of ligations were then prepared using plasmids pADGal4 (7.6 kb) and pCMV-Script (4.3 kb) as vectors. These plasmids were digested with EcoRI and XhoI. Approximately 10 ng of a mouse brain cDNA library (prepared using Stratagene's cDNA synthesis kit) was ligated to 30 ng of pCMV-Script (or 60 ng of pADGal4). The ligation reactions proceeded overnight at 4°, C. and were subsequently transformed into XL10-GOLD, DH10B, and XL2-Blue. Data for both experiments are shown in Table 3. The results indicated that XL10-GOLD, which was approximately 5 fold better at transforming pUC DNA, and was about 20–40 fold better at transforming the ligated (i.e., larger) DNA molecules than was DH10B. The observed difference is very significant in cloning applications such as cDNA library construction or PCR cloning, and represents another of the particularly useful features of cells harboring the Hte⁻ mutation.

TABLE 3

Transformations With cDNA Libraries In Two Plasmic Vectors

|  | pUC | pADGal4 | pCMV-Script |
|---|---|---|---|
| DH10B | $1.0 \times 10^9$ | $2.0 \times 10^3$ | $2.3 \times 10^4$ |
| GOLD | $5.0 \times 10^9$ | $5.0 \times 10^4$ | $4.0 \times 10^5$ |
| XL2-Blue | $5.0 \times 10^9$ | $1.0 \times 10^4$ | $8.0 \times 10^4$ |

Library 1: pADGal4, a pBluescript derived plasmid (7.6 kb) was digested with EcoRI and XhoI. 60 ng of the digested vector were ligated to 10 ng of cDNA as above. Transformations were performed in the same manner and the number of Ampicillin resistant transformants were counted.

Library 2: pCMV-Script, a pBluescript derived plasmid (4.3 kb) was digested with EcoRI and XhoI. 30 ng of the digested vector were ligated to 10 ng of cDNA that was prepared by a standard protocol. The DNA was ligated overnight at 4° C. in a 10 µl volume and 1 µl was added to competent cells from the indicated strains.

The specifics of the preferred method of transforming XL10-GOLD is as follows:

1. Aliquot 100 µl of cells in a Falcon 2059 tube.
2. Add β-mercaptoethanol to a final concentration of 50 mM (2 µl).
3. Add NaCl to a final concentration of 110 mM (2 µl).
4. Incubate tubes on ice for 10 minutes.
5. Add DNA.
6. Incubate on ice for 30 minutes.
7. Heat pulse at 42° C. for 30 seconds.
8. Incubate tubes on ice for 2 minutes.
9. Add 0.9 ml of prewarmed NZY media and incubate at 37° C. for 60 minutes shaking at 225–250 rpm.
10. Plate aliquots as desired and incubate overnight at 37° C.

EQUIVALENTS

All publications and patents mentioned in the above specification are herein incorporated by reference. The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

What is claimed is:

1. An isolated strain of gram negative bacteria comprising an Hte mutation included in the strain deposited as ATCC No. 55962 and having more efficient transformation with foreign plasmids than gram negative bacteria that lack said Hte mutation.

2. The isolated strain of claim 1, wherein the isolated strain is a bacteria selected from: a species of the genus *Pseudomonas*; a species of the genus *Rhizobium*; a species of the genus *Agrobacterium*; a species of the genus *Salmonella*; a species of the genus *Proteus*; a species of the genus *Shigella*; or a species of the genus *Kiebsiella*.

* * * * *